United States Patent
Zou et al.

(10) Patent No.: US 9,371,262 B2
(45) Date of Patent: Jun. 21, 2016

(54) ONE-STEP INTERMOLECULAR ELECTROCYCLIC REARRANGEMENT PROCESS

(71) Applicant: Givaudan S.A., Vernier (CH)

(72) Inventors: Yue Zou, Shanghai (CN); Li Jun Zhou, Zhuji (CN); Changming Ding, Shanghai (CN); Andreas Goeke, Winterthur (CH)

(73) Assignee: Givaudan S.A., Vernier (CH)

( * ) Notice: Subject to any disclaimer, the term of this patent is extended or adjusted under 35 U.S.C. 154(b) by 59 days.

(21) Appl. No.: 14/353,562

(22) PCT Filed: Oct. 26, 2012

(86) PCT No.: PCT/EP2012/071215
§ 371 (c)(1),
(2) Date: Apr. 23, 2014

(87) PCT Pub. No.: WO2013/060818
PCT Pub. Date: May 2, 2013

(65) Prior Publication Data
US 2014/0288326 A1    Sep. 25, 2014

(30) Foreign Application Priority Data

Oct. 27, 2011   (WO) ................ PCT/CN2011/081437

(51) Int. Cl.
| | |
|---|---|
| *C07C 45/54* | (2006.01) |
| *C07C 209/08* | (2006.01) |
| *C07C 231/10* | (2006.01) |
| *C07C 259/06* | (2006.01) |
| *C07C 67/475* | (2006.01) |
| *C07D 313/00* | (2006.01) |
| *C07D 217/06* | (2006.01) |
| *C07D 225/02* | (2006.01) |
| *C07D 471/04* | (2006.01) |
| *C07D 487/04* | (2006.01) |
| *C07D 209/08* | (2006.01) |
| *C07D 211/16* | (2006.01) |
| *C11B 9/00* | (2006.01) |
| *C07B 41/12* | (2006.01) |

(52) U.S. Cl.
CPC ................ *C07C 45/54* (2013.01); *C07B 41/12* (2013.01); *C07C 67/475* (2013.01); *C07C 231/10* (2013.01); *C07C 259/06* (2013.01); *C07D 209/08* (2013.01); *C07D 211/16* (2013.01); *C07D 217/06* (2013.01); *C07D 225/02* (2013.01); *C07D 313/00* (2013.01); *C07D 471/04* (2013.01); *C07D 487/04* (2013.01); *C11B 9/003* (2013.01); *C11B 9/0015* (2013.01); *C11B 9/0019* (2013.01); *C11B 9/0034* (2013.01); *C11B 9/0049* (2013.01); *C11B 9/0084* (2013.01); *C11B 9/0092* (2013.01); *C07C 2101/16* (2013.01); *C07C 2102/20* (2013.01)

(58) Field of Classification Search
CPC .... C07C 45/54; C07C 67/475; C07C 209/08; C07C 231/10; C07B 41/12
USPC .................................. 560/174, 177, 179, 183
See application file for complete search history.

(56) References Cited

PUBLICATIONS

Esteve, et al., "Highly Stereoselective Titanium-Mediated Aldo Reactions from Chiral alpha-Silyloxy Ketones. A Reliable Tool for the Synthesis of Natural Products", Tetrahedron, Jun. 9, 2011, pp. 6045-6056, vol. 67, No. 33.*
Wong, et al., "Recombinant 2-Deoxyribose-5-Phosephate Aldolase in Organic Synthesis: Use of Sequential Two-Substrate and Three-Substrate Aldol Reactions", Journal of the American Chemical Society, Mar. 22, 1995, pp. 3333-3339, vol. 117, No. 11.*
Wong et al, JACS (1995), vol. 117(12), p. 3333.*
PCT/EP2012/071215—International Search Report, Feb. 4, 2013.
PCT/EP2012/071215—International Written Opinion, Feb. 4, 2013.
PCT/EP2012/071215—International Preliminary Report on Patentability, Apr. 29, 2014.
PCT/CN2011/081437—International Search Report, Aug. 2, 2012.
PCT/CN2011/081437—International Written Opinion, Aug. 2, 2012.
PCT/CN2011/081437—International Preliminary Report on Patentability, Apr. 29, 2014.
Esteve, et al., "Highly Stereoselective Titanium-Mediated Aldo Reactions from Chiral alpha-Silyloxy Ketones. A Reliable Tool for the Synthesis of Natural Products", Tetrahedron, Jun. 9, 2011, pp. 6045-6056, vol. 67, No. 33, Elsevier Science Publishers, Amsterdam, NL.
Liu, et al., "Organocatalytic and Highly Stereoselective Direct Vinylogous Mannich Reaction", Journal of the American Chemical Society, Feb. 1, 2007, pp. 1878-1879, vol. 129, No. 7.
Nicolaou, et al., "An Approach to Epothilones Based on Olefin Metathesis", Angewandte Chemie, 1996, pp. 2399-2401, vol. 35, No. 20.
Padwa, et al., "A New Construct of the CIS-3a-aryloctahydroindole Skeleton Via the [4+2] Cycloaddition of Furanyl Carbamates", Heterocycles, 2002, pp. 227-242, vol. 58.
Schneider, et al., "Catalytic Use of Indium(0) for Carbon-Carbon Bond Transformations in Water: General Catalytic Allylations of Ketones with Allylboronates", Journal of the American Chemical Society, Oct. 22, 2008, pp. 13824-13825, vol. 130, No. 42.

* cited by examiner

*Primary Examiner* — Kamal Saeed
*Assistant Examiner* — Janet L Coppins
(74) *Attorney, Agent, or Firm* — Curatolo Sidoti Co., LPA; Joseph G. Curatolo; Salvatore A. Sidoti

(57) ABSTRACT

A direct acid catalyzed intermolecular electrocyclic rearrangement process for the preparation of linear and cyclic homoallylic ester and amides. A one step intermolecular electrocyclic rearrangement process includes the step of reacting a beta, gamma-unsaturated aldehyde or ketone, in which the beta, gamma-unsaturation is not part of an aromatic ring, with another aldehyde or a secondary aldimine in the presence of an acid.

15 Claims, No Drawings

ONE-STEP INTERMOLECULAR ELECTROCYCLIC REARRANGEMENT PROCESS

CROSS REFERENCE TO RELATED APPLICATIONS

This application is a national stage application of International Application No. PCT/EP2012/071215, filed 26 Oct. 2012, which claims priority from International Patent Application No. PCT/CN2011/081437, filed 27 Oct. 2011, from which applications priority is claimed, and which are incorporated herein by reference.

The present invention refers to a novel process for the preparation of linear and cyclic homoallylic ester and amides, which constitutes a valuable class of organic compounds.

PRIOR ART

Such compounds can be prepared by multistage syntheses which are essentially based on five basic methods known in the art:

a) By addition of an allyl metal species to a carbonyl compound and imino groups resulting in homoallyl alcohols or amines, followed by esterification or amide formation.

b) By carbonyl ene or Conia ene reactions to homoallylic alcohols, followed by esterification.

c) By imino ene reactions to homoallyl amine derivatives, followed by subsequent transformation which lead to amide formation.

d) By metal hydride catalyzed addition of dienes to carbonyl compounds, followed by esterification.

e) By 2,3-Wittig rearrangements of allyl benzyl or diallyl ethers and aza-Wittig rearrangements resulting in homoallyl alcohols and amines respectively, followed by esterification and amide formation.

All the prior art syntheses have in common that the preparation of the esters and amides respectively take place in two sub-sequential steps, this means that in a first step a homoallylic alcohol or amine is formed which is subsequently transformed into an ester or amide derivative, respectively.

DESCRIPTION OF THE INVENTION

One object of the present invention is a simple and cost-effective method for producing linear and cyclic homoallylic ester and amides as herein below described.

One embodiment of the present invention is the direct acid catalyzed intermolecular electrocyclic rearrangement of β,γ-unsaturated aldehydes or ketones with another aldehyde to afford esters or lactones of homoallylic alcohols in one process step. The β,γ-unsaturation is not part of an aromatic ring.

A further embodiment of the present invention is the direct acid catalyzed intermolecular electrocyclic rearrangement of β,γ-unsaturated aldehydes or ketones with secondary aldimines to form amides or lactames of homoallylic amines in one process step. The β,γ-unsaturation is not part of an aromatic ring.

Surprisingly it was found that, in the presence of a catalyst, β,γ-unsaturated carbonyl compounds (A) react with another carbonyl compound (B wherein X=O) or a derivative like an imine or oxime ether (B wherein X=NR⁷) to homoallylic compounds (I). It is believed, without to be bound by theory that this reaction proceeds via an intermolecular electrocyclic rearrangement that involves an activated homoallylic aldehyde/Lewis acid (LA) complex C'which rearranges via intermediate of formula (C'') to form a compound of formula (I), as depicted in Scheme 1 below. The stabilization of positive charge by substituents in the intermediate (C'') is beneficial for a smooth conversion of the starting compound of formula (A) to the rearranged compound of formula (I).

Scheme 1: rearrangement reaction

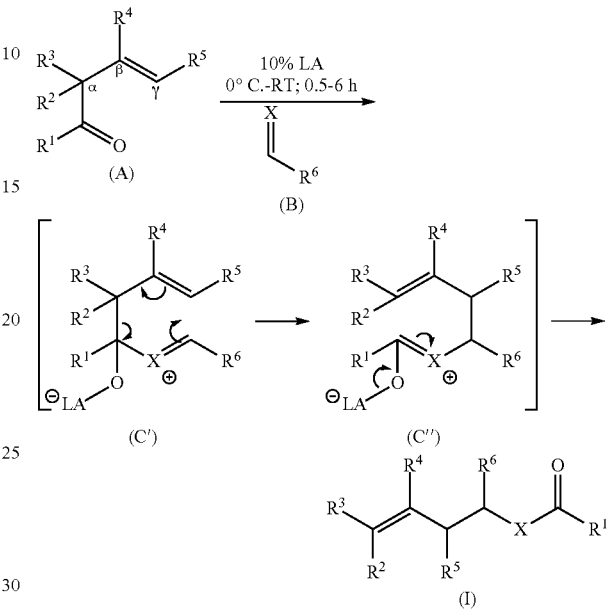

As used herein, the term "secondary aldimines" denotes for imines in analogy to aldehydes wherein the carbonyl oxygen atom is replaced by RN= group with R is not hydrogen (i.e. R is alkyl).

Non limiting examples are secondary aldimines selected from acetaldehyde O-methyl oxime, acetaldehyde O-ethyl oxime, hexanal O-methyl oxime, hexanal O-ethyl oxime, 3-methylbut-2-enal O-ethyl oxime, benzaldehyde O-methyl oxime, 2,3,4,5-tetrahydropyridine, indole, 3,4-dihydro2H-pyrrole, N-butylidenebutan-1-amine, and 3-(methyleneamino) propanoates, such as ethyl 3-(methleneamino)propanoate.

In another embodiment there is provided a method of producing homoallylic compounds of formula (I)

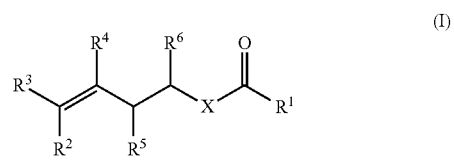

by an intermolecular electrocyclic rearrangement of a beta, gamma-unsaturated carbonyl compound of formula (A)

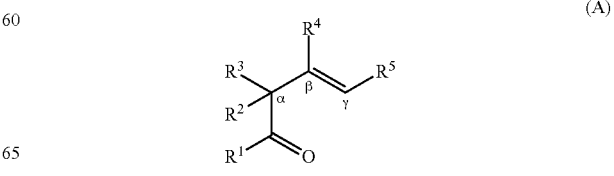

with a compound of formula (B)

wherein

X is oxygen or

X is $NR^7$, wherein $R^7$ is selected from $C_1$-$C_8$ alkyl (e.g. butyl, isoamyl), $C_6$-$C_8$ aryl, $C_1$-$C_2$ alkoxy, $C_1$-$C_8$ alkyl comprising one carbonyloxy group (—C(O)O—); or $R^6$ and $R^7$ may form together with the atoms to which they are attached a 5-10 membered mono- or bi-cyclic ring (e.g. compound B is selected from 3,4-dihydro2H-pyrrole, 3H-indole, or 2,3,4,5-tetrahydropyridine);

$R^1$ is selected from hydrogen, methyl and phenyl;

$R^2$ is selected from hydrogen, a hydrocarbon group selected from $C_1$-$C_8$ alkyl (e.g. methyl), $C_2$-$C_8$ alkenyl (e.g. 3-methyl-pent-4-enyl), $C_6$-$C_8$ aryl, and $C_1$-$C_3$ alkyl $C_6$-$C_8$ aryl (e.g. benzyl), wherein the hydrocarbon group optionally comprises one functional group selected from methoxy, —C(O)—, and —OC(O)—;

$R^3$ is selected from hydrogen and methyl;

or $R^1$ and $R^2$ or $R^1$ and $R^3$ form together a bivalent linear $C_3$-$C_{16}$ alkyl or alkenyl (e.g. —(CH$_2$)$_3$—, —(CH$_2$)$_4$—, —(CH$_2$)$_5$—, —(CH$_2$)$_6$—, —(CH$_2$)$_7$—, —(CH$_2$)$_{10}$—, —CH═CH—CH$_2$—), wherein the alkyl/alkenyl chain may be optionally substituted with one or more methyl or ethyl groups; or $R^2$ and $R^3$ form together with the carbon atom to which they are attached a $C_5$-$C_8$ cycloalkyl ring or $C_5$-$C_8$ cycloalkenyl ring (e.g. $C_6$ cycloalkenyl), the ring is optionally substituted with one or more $C_1$-$C_4$ alkyl or alkenyl groups (e.g. with two alkyl groups);

$R^4$ is selected from hydrogen, methyl and ethyl;

$R^5$ is selected from hydrogen, $C_1$-$C_5$ alkyl or alkenyl (e.g. methyl, ethyl) and $C_2$-$C_5$ alkenyl (e.g. 1-propenyl);

or $R^4$ and $R^5$ form together a bivalent $C_3$-$C_6$ alkyl or alkenyl (e.g. —(CH$_2$)$_3$—, —(CH$_2$)$_4$—, and —(CH$_2$)$_5$—, —CH═CH—CH$_2$—);

or $R^5$ and $R^2$ or $R^5$ and $R^3$ form together with the carbon atoms to which they are attached a 5-12 membered hydrocarbon ring (e.g. a 6-membered ring);

$R^6$ is selected from H, $C_1$-$C_8$ alkyl (e.g. iso-butyl, tert-butyl, n-butyl, n-propyl, iso-propyl, hexyl), $C_2$-$C_8$ alkenyl (e.g. isobutenyl) and $C_6$-$C_8$ aryl wherein the aryl is optionally substituted with one or more groups selected from methyl, methoxy, ethoxy, acetoxy, hydroxy, and 1,3-dioxol;

in the presence of a Lewis acid or Brønsted acid.

Non limiting examples are compounds of formula (B) wherein X is oxygen selected from acetaldehyde, propionaldehyde, isobutyraldehyde, butyraldehyde, pivalaldehyde, hexanal, heptanal, and 3-methylbutanal, anisaldehyde, heliotropin (benzo[d][1,3]dioxole-5-carbaldehyde) and vanillin.

As used in relation to compounds of formula (I) and formula (A) respectively, unless otherwise indicated, "hydrocarbon ring" refers to cycloalkly rings comprising none, one or more double bonds, the ring being optionally substituted with one or more $C_1$-$C_4$ alkyl groups, such as methyl, ethyl, and iso-propyl. For example, hydrocarbon rings comprising 5, 6, 7, 8, 9, 10, or 11 ring members, the ring may be further substituted with one ethyl group, or one, two or three methyl groups.

As used in relation to the compounds of formula (I), (A) and (B), unless otherwise indicated, "alkyl" and "alkenyl" refers to linear and branched alkyl and linear and branched alkenyl.

Non limiting examples are beta, gamma-unsaturated carbonyl compounds of formula (A) selected from 2,4-dimethyl-1-(prop-1-en-2-yl)cyclohex-3-enecarbaldehyde, 1-(prop-1-en-2-yl)cyclohex-3-enecarbaldehyde, 1-vinylcyclohex-3-enecarbaldehyde, 6-methyl-3-(prop-1-en-2-yl)oct-7-en-2-one, 5-acetyl-6-methylhept-6-en-2-yl acetate, 2-(prop-1-en-2-yl)cyclopentanone, [1,1'-bi(cyclopentan)]-1'-en-2-one, 1-methyl-[1,1'-bi(cyclopentan)]-1'-en-2-one, 2-(prop-1-en-2-yl)cyclododecanone, 1-(4,7,7-trimethylbicyclo[4.1.0]hept-4-en-3-yl)ethanone, 3,3,4-trimethylpent-4-en-2-one, 2-(prop-1-en-2-yl)cyclohexanone, 2-(prop-1-en-2-yl)cycloheptanone, 2-(prop-1-en-2-yl)cyclooctanone, 2-(prop-1-en-2-yl)cyclododecanone, 2-benzyl-2-methylpent-3-enal, 2,5-dimethyl-2-(prop-1-en-2-yl)cyclohexanone, 2-(prop-1-en-2-yl)cyclononanone, 2,6,6-trimethylcyclohex-2-enecarbaldehyde, and 4-ethyl-2-(prop-1-en-2-yl)cyclohexanone.

Non limiting examples are homoallylic esters and amides of formula (I) selected from 4-(2,4-dimethylcyclohex-3-en-1-ylidene)pentan-2-yl formate, 5-(cyclohex-3-en-1-ylidene)-2-methylhexan-3-yl formate, 4-(cyclohex-3-en-1-ylidene)butan-2-yl formate, 4,8-dimethyldeca-4,9-dien-2-yl acetate, (E)-4-methylnon-4-ene-2,8-diyl diacetate, rac-(Z)-7,9-dimethyl-4,5,8,9-tetrahydrooxonin-2(3H)-one, rac-(Z)-1,7-Dimethyl-5,6,8,9,10,10a-hexahydro-1H-cyclopenta[c]oxonin-3(4H)-one, rac-(E)-14,16-Dimethyloxacyclohexadec-13-en-2-one, (S)-1-((1R,2S,6R)-3,7,7-Trimethylbicyclo[4.1.0]hept-3-en-2-yl)ethyl acetate, 2,3-Dimethylundec-2-en-5-yl acetate, N-(4,5-dimethylhex-4-en-2-yl)-N-methoxyacetamide, N-(2,3-dimethyldec-2-en-5-yl)-N-methoxyacetamide, N-(4,5-dimethylhex-4-en-2-yl)-N-ethoxyacetamide, N-methoxy-N-(2,6,7-trimethylocta-2,6-dien-4-yl)acetamide, N-(3,4-dimethyl-1-phenylpent-3-en-1-yl)-N-methoxyacetamide, 1-(2-(2,3-dimethylbut-2-en-1-yl)indolin-1-yl)ethanone, (E)-1-methoxy-8,10-dimethyl-3,4,5,6,9,10-hexahydroazecin-2(1H)-one, (E)-1-ethoxy-8,10-dimethyl-3,4,5,6,9,10-hexahydroazecin-2(1H)-one, (E)-1-methoxy-8-methyl-10-pentyl-3,4,5,6,9,10-hexahydroazecin-2(1H)-one, (E)-12-methyl-7,8,9,10,13a,14-hexahydroazecino[1,2-a]indol-6(13H)-one, (E)-1-methoxy-9,11-dimethylazacycloundec-8-en-2-one, (E)-1-ethoxy-9,11-dimethylazacycloundec-8-en-2-one, (E)-1-methoxy-10-methyl-12-pentylazacyclododec-9-en-2-one, (E)-1-methoxy-10,12-dimethylazacyclododec-9-en-2-one, (E)-1-ethoxy-10,12-dimethylazacyclododec-9-en-2-one, (E)-1-methoxy-14,16-dimethylazacyclohexadec-13-en-2-one, (E)-1-ethoxy-14,16-dimethylazacyclohexadec-13-en-2-one, N-(2,4-dimethyl-1-phenyldec-2-en-5-yl)-N-methoxyformamide (4S,E)-1-butyl-4,7,8-trimethyl-10-propyl-3,4,5,6,9,10-hexahydroazecin-2(1H)-one,
(E)-12-methyl-3,4,7,8,9,10,13,13a-octahydro-1H-pyrido[1,2-a]azecin-6(2H)-one,
1-(2-(2,3-dimethylbut-2-en-1-yl)piperidin-1-yl)ethanone, and
ethyl 3-(11-methyl-2-oxoazacyclotridec-10-en-1-yl)propanoate.

Lewis acids may be selected from all types of Lewis acids, well known to the skilled person. Suitable acids are, for example, BF$_3$Et$_2$O, SnCl$_4$, TiCl$_4$, AlCl$_3$, EtAlCl$_2$, FeCl$_3$, ZnBr$_2$ and H$^{\oplus}$. Brønsted acids are well known to the skilled person. Examples are p-TsOH, H$_2$SO$_4$, and CF$_3$SO$_3$H.

The concentration of the acid is not critical and may vary from about 0.5 mol % to about 120 mol %. However it was observed that the reaction described herein above is a catalytic reaction when esters or lactones are formed (i.e. for compounds of formula (I) wherein X is oxygen). By catalytic reaction is meant, that about 0.5 mol % to about 20 mol % of an acid (e.g. about 10 mol %) is sufficient enough to drive the conversion to completion. Even though low concentrations of acid are sufficient enough, higher concentrations may have an influence on the reaction rate and thus be preferred. The optimum concentration may be easily established by routine experimentation in every case.

The reaction temperature applied is not really critical either. The intermolecular electrocyclic rearrangement takes place in a broad temperature range, e.g. from −80° C. to 120° C., such as from −10° C. to about 80° C., (for example about 0° C. to room temperature (i.e. about 20-25° C.), or 50° C. to about 80° C.).

Beta substituted beta, gamma-unsaturated carbonyl compound, i.e. compounds of formula (A) wherein R$^4$ is not hydrogen, were found to undergo the reaction described hereinabove much faster and with higher yields compared to compounds of formula (A) wherein R$^4$ is hydrogen.

Using the method described hereinabove it was possible to produce not only known compounds, such as derivatives of 1,3-dimethyl-but-3-en-1-yl formate, e.g. 1,3-dimethyl-but-3-en-1-yl isobutyrate=4-methylpent-4-en-2-yl isobutyrate (CAS 80118-06-5) or 1-(3,7,7-trimethylbicyclo[4.1.0]hept-3-en-2-yl)ethyl acetate (CAS 29583-31-1) but also compounds not described in the literature such as 4-(2,4-dimethylcyclohex-3-en-1-ylidene)pentan-2-yl formate, 5-(cyclohex-3-en-1-ylidene)-2-methylhexan-3-yl formate, 4,8-dimethyldeca-4,9-dien-2-yl acetate, 1-(3,7,7-Trimethyl-bicyclo[4.1.0]hept-3-en-2-yl)ethyl acetate and 1-methoxy-8,10-dimethyl-3,4,5,6,9,10-hexahydroazecin-2(1H)-one.

In a particular embodiment there is provided a method of preparing lactones starting from compounds of formula (A) wherein X is oxygen and R$^1$ and R$^2$ or R$^3$ form together a bivalent C$_3$-C$_{10}$ alkyl or alkenyl group, resulting in a ring-enlargement [n+4] lactone (I), as depicted in Scheme 2 below.

Scheme 2: lactone ring-enlargement rearrangement

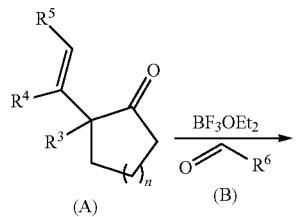

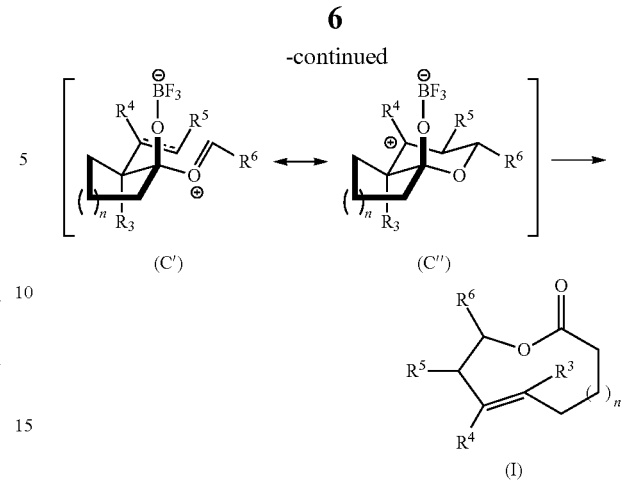

In a further embodiment there is provided a method of preparing lactames starting from compounds of formula (A) wherein X is NR$^7$, and R$^1$ and R$^2$ or R$^3$ form together a bivalent C$_3$-C$_{16}$ alkyl or alkenyl group, resulting in a ring-enlargement [n+4] lactam, as depicted in Scheme 3 below.

Scheme 2: lactam ring-enlargement rearrangement

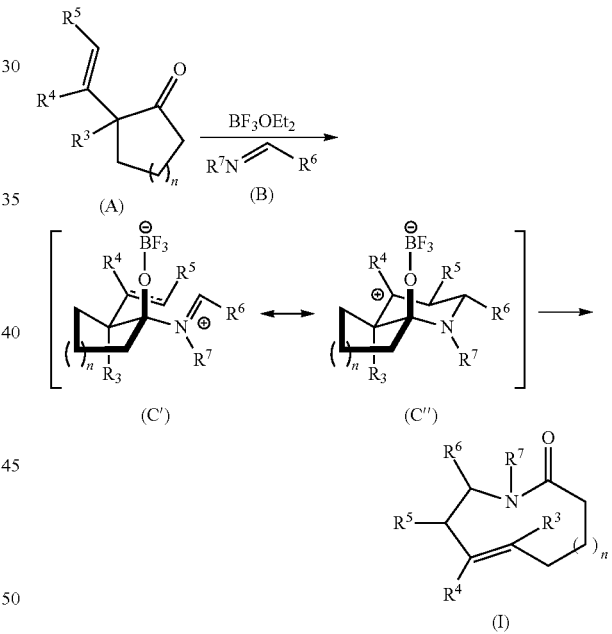

Using the method described herein there is provided a new process for medium size (8-12 membered ring, e.g. 9, 10, or 11 membered ring) to macro size (13-20 membered rings) lactones and lactames. In particular medium sized lactones are difficult to prepare with methods known to the skilled person and thus the process described herein constitutes a real alternative for the preparation of medium to macro size lactones.

In a further embodiment there is provided a method of producing homoallylic compounds of formula (I) wherein R$^1$ is selected from hydrogen, methyl and phenyl, and R$^2$ and R$^3$ form together with the carbon atom to which they are attached a C$_5$-C$_8$ cycloalkyl ring or C$_5$-C$_8$ cycloalkenyl ring (e.g. C$_8$ cycloalkenyl), the ring is optionally substituted with one or more $C_1$-$C_4$ alkyl or alkenyl groups (e.g. with two alkyl groups), $R^4$ is selected from hydrogen, methyl and ethyl, and $R^5$ is hydrogen or methyl.

In a further embodiment there is provided a method of producing homoallylic compounds of formula (I) wherein $R^3$ is hydrogen, $R^4$ is selected from hydrogen, methyl and ethyl, $R^5$ is hydrogen or methyl, and $R^1$ and $R^2$ form together a bivalent $C_3$-$C_{16}$ alkyl ($R^1$ and $R^2$ form together —$(CH_2)_3$—, —$(CH_2)_4$—, —$(CH_2)_5$—, —$(CH_2)_6$—, or —$(CH_2)_{10}$—.)

The beta, gamma-unsaturated carbonyl compound of formula (A) may be easily prepared by art-recognized methods.

The linear and cyclic homoallylic ester and amides of formula (I) produced in accordance with the invention may be odorant compounds as such. They are also valuable intermediates or precursors for the preparation of other chemical compounds suitable as fragrance, pharmaceutical and/or agrochemical.

The invention is now further described with reference to the following non-limiting examples. These examples are for the purpose of illustration only and it is understood that variations and modifications can be made by one skilled in the art.

EXAMPLE 1

4-(2,4-dimethylcyclohex-3-en-1-ylidene)pentan-2-yl formate

An argon flushed three-necked flask which was cooled by an ice-water bath was charged with β,γ-unsaturated carbonyl compound A (2,4-dimethyl-1-(prop-1-en-2-yl)cyclohex-3-enecarbaldehyde, mixture of syn and anti in a ratio of 4:1; 1.78 g, 10 mmol), aldehyde B (acetaldehyde, 0.53 g, 12 mmol) and 1,2-dichloroethane (20 mL). Boron trifluoride etherate (0.14 g, 1.0 mmol) were added dropwise under argon. After completion of the addition the ice-water bath was removed and the mixture was stirred for 2 hours at room temperature. The completion of reaction was checked by GC analysis of reaction aliquots quenched with a solution of saturated $NaHCO_3$ in water. After complete conversion (>95%), the reaction mixture was quenched with sat. aqueous $NaHCO_3$ solution (10 mL). The organic phase was separated and the aqueous layer was extracted with MTBE three times. The combined organic layers were washed with brine (20 mL), dried ($MgSO_4$) and evaporated in vacuo. The residue was purified by column chromatography on silica gel (MTBE/hexane=1:20) to yield the title product (1.55 g, 70%) as colorless liquid. Mixture of four isomers in a ratio of 1:2:3:16.

$^1$H NMR (300 MHz, $CDCl_3$): δ=7.99 (s, 1H, —OCHO), 5.32-5.26 (m, 1H), 5.21-5.10 (m, 1H), 3.10-2.95 (m, 1H), 2.65-2.57 (m, 1H), 2.50 (dd, J=7.5, 13.5 Hz, 1H), 2.18 (dd, J=7.5, 13.5 Hz, 1H), 2.09-1.86 (m, 3H), 1.70 (s, 3H, CH3), 1.66 (s, 3H, CH3), 1.25 (d, J=6.3 Hz, 3H), 0.98 (d, J=7.0 Hz, 3H) ppm. Major isomer: $^{13}$C NMR (75 MHz, $CDCl_3$): δ=160.6 (d), 137.2 (s), 133.3 (s), 126.9 (d), 121.1 (s), 69.9 (d), 40.3 (t), 33.5 (d), 31.7 (t), 23.3 (q), 23.3 (t), 20.4 (q), 19.9 (q), 18.4 (q) ppm. GC/MS (EI): 222 ($M^+$, 27), 176 (14), 161 (100), 147 (7), 135 (51), 119 (71), 107 (59), 91 (41), 77 (18), 41 (22). IR (neat, v/cm$^{-1}$): 2961, 2903, 1721, 1451, 1378, 1177. HRMS (ESI): m/z: calcd. for $C_{14}H_{22}O_2$ (M+Na)$^+$ 245.1517. Found: 245.1510.

Odour description: lactonic, slight milk, sweet, very metallic

EXAMPLE 2

5-(cyclohex-3-en-1-ylidene)-2-methylhexan-3-yl formate

Following the general procedure as described in Example 1, 1-(prop-1-en-2-yl)cyclohex-3-enecarbaldehyde (1.50 g, 10 mmol), isobutyraldehyde (0.86 g, 12 mmol) and boron trifluoride etherate (0.14 g, 1.0 mmol) in 1,2-dichloroethane (10 mL) were reacted to give the title product as a colorless liquid (1.55 g, 70% yield). Mixture of E/Z isomers in a ratio 2:1.

$^1$H NMR (300 MHz, $CDCl_3$): δ=8.03, 7.99 (s, 1H, —OCHO), 5.80-5.60 (m, 2H), 5.02-4.89 (m, 1H), 2.92-2.65 (m, 2H), 2.60-2.45 (m, 1H), 2.43-1.99 (m, 5H), 1.92-1.75 (m, 1H), 1.71, 1.68 (s, 3H, CH3), 0.95 (d, J=6.7 Hz, 6H, —CH(CH3)$_2$) ppm. $^{13}$C NMR (75 MHz, $CDCl_3$): δ=160.8, 160.7 (d), 132.0, 131.7 (s), 127.2, 126.9 (d), 126.9, 126.6 (d), 121.9, 121.6 (s), 77.3, 76.9 (d), 36.2, 35.7 (t), 31.8, 31.5 (d), 29.9, 29.8 (t), 27.1, 26.8 (t), 26.9, 26.6 (t), 18.9, 18.8 (q), 18.7, 18.0 (q), 17.5, 17.4 (q) ppm. GC/MS (EI): 222 ($M^+$, 1), 176 (26), 161 (15), 147 (1), 133 (100), 120 (18), 105 (67), 91 (59), 79 (46), 67 (9), 55 (26), 41 (21). IR (neat, v/cm$^{-1}$): 3025, 2965, 2913, 1721, 1467, 1388, 1169. HRMS (ESI): m/z: calcd. for $C_{14}H_{22}O_2$ (M+Na)$^+$ 245.1517. Found: 245.1501.

Odour description: green geranium, slightly floral cinnamic fruity.

EXAMPLE 3

4-(cyclohex-3-en-1-ylidene)butan-2-yl formate

Following the general procedure as described in Example 1, 1-vinylcyclohex-3-enecarbaldehyde (1.50 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (0.72 g, 40% yield). Mixture of E/Z isomers in a ratio 1:1.

$^1$H NMR (300 MHz, $CDCl_3$): δ=8.03, (s, 1H, —OCHO), 5.78-5.58 (m, 2H), 5.27-5.11 (m, 1H), 5.07-4.95 (m, 1H), 2.80-2.68 (m, 2H), 2.46-2.22 (m, 4H), 2.17-2.05 (m, 2H), 1.25 (d, J=6.2 Hz, 3H, CH3) ppm. $^{13}$C NMR (75 MHz, $CDCl_3$): δ=160.7 (d), 138.9, 138.8 (s), 127.3, 126.8 (d), 126.7, 125.6 (d), 117.0, 116.2 (d), 71.0, 70.9 (d), 35.4, 33.7 (t), 33.2, 33.0 (t), 28.1, 27.2 (t), 27.0, 25.4 (t), 19.5, 19.4 (q) ppm. GC/MS (EI): 180 ($M^+$, 1), 162 (1), 134 (73), 119 (54), 105 (51), 91 (92), 79 (100), 65 (12), 45 (23). IR (neat, v/cm$^{-1}$): 3026, 2911, 1719, 1448, 1176. HRMS (ESI): m/z: calcd. for $C_{11}H_{16}O_2$ (M+Na)$^+$ 203.1048. Found: 203.1039.

EXAMPLE 4

4,8-dimethyldeca-4,9-dien-2-yl acetate

Following the general procedure as described in Example 1, 6-methyl-3-(prop-1-en-2-yl)oct-7-en-2-one (1.80 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (1.90 g, 85% yield). Mixture of 2 isomers in a ratio 1:5.

$^1$H NMR (300 MHz, $CDCl_3$): δ=5.78-5.60 (m, 1H), 5.27-5.12 (m, 1H), 5.04 (dd, J=6.5, 12.9 Hz, 1H), 5.00-4.87 (m, 2H), 2.45-2.22 (m, 1H), 2.18-1.92 (m, 7H), 1.70, 1.61 (s, 3H, CH3), 1.37-1.26 (m, 2H), 1.18 (d, J=6.2 Hz, 3H), 0.98 (d, J=6.7 Hz, 3H) ppm. Major E-isomer: $^{13}$C NMR (75 MHz, $CDCl_3$): δ=170.4 (s), 144.5 (d), 130.9 (s), 127.9 (d), 112.6 (t), 69.1 (d), 46.3 (t), 37.3 (d), 36.5 (t), 25.6 (t), 21.2 (q), 20.1 (q), 19.7 (q), 16.1 (q) ppm. GC/MS (EI): 224 ($M^+$, 1), 164 (5), 149 (20), 135 (10), 121 (14), 109 (22), 95 (57), 81 (33), 67 (33), 55 (23), 43 (100). IR (neat, v/cm$^{-1}$): 2969, 1734, 1453, 1373, 1242.

Odour description: floral, fruity, myraldyl violet.

EXAMPLE 5

(E)-4-methylnon-4-ene-2,8-diyl diacetate

Following the general procedure as described in Example 1, 5-acetyl-6-methylhept-6-en-2-yl acetate (2.12 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (2.41 g, 94% yield). Mixture of 4 isomers in a ratio of 1:1:3:3.

$^1$H NMR (300 MHz, CDCl$_3$): δ=5.23-5.11 (m, 1H), 5.09-4.98 (m, 1H), 4.94-4.80 (m, 1H), 2.45-2.20 (m, 1H), 2.16-1.98 (m, 9H), 1.73-1.43 (m, 5H), 1.26-1.13 (m, 6H) ppm. Two major isomers: $^{13}$C NMR (75 MHz, CDCl$_3$): δ=170.6 (s), 170.4 (s), 131.9, 131.8 (s), 126.7, 126.6 (d), 70.4 (d), 69.0 (d), 46.2 (t), 35.7, 35.6 (t), 23.9, 23.8 (t), 21.3 (q), 21.2 (q), 19.9 (q), 19.7 (q), 16.0 (q) ppm. GC/MS (EI): 256 (M$^+$, 1), 136 (38), 121 (43), 107 (100), 95 (24), 79 (13), 68 (16), 55 (8), 43 (84). IR (neat, ν/cm$^{-1}$): 2977, 1732, 1449, 1371, 1238. HRMS (ESI): m/z: calcd. for C$_{14}$H$_{24}$O$_4$ (M+Na)$^+$ 279.1572. Found: 279.1577.

EXAMPLE 6 rac-(Z)-7,9-dimethyl-4,5,8,9-tetrahydrooxonin-2(3H)-one

Following the general procedure as described in Example 1, 2-(prop-1-en-2-yl)cyclopentanone (1.24 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (0.59 g, 35% yield). Single Z-isomer.

$^1$H NMR (300 MHz, CDCl$_3$): δ=5.23-5.13 (m, 1H), 5.07-4.94 (m, 1H), 2.52 (dd, J=12.5, 12.5 Hz, 1H), 2.46-2.35 (m, 1H), 2.34-2.16 (m, 2H), 2.10-1.96 (m, 2H), 1.85-1.75 (m, 1H), 1.76 (d, J=12.5 Hz, 1H), 1.71 (s, 3H, CH3), 1.31 (d, J=6.4 Hz, 3H, CH3) ppm. $^{13}$C NMR (75 MHz, CDCl$_3$): δ=174.6 (s), 132.0 (s), 128.8 (d), 68.6 (d), 41.3 (t), 33.4 (t), 27.1 (t), 25.8 (t), 25.3 (q), 20.4 (q) ppm. GC/MS (EI): 168 (M$^+$, 13), 124 (22), 109 (8), 96 (100), 81 (33), 68 (32), 55 (26), 41 (16).

EXAMPLE 7 rac-(Z)-1,7-Dimethyl-5,6,8,9,10,10a-hexahydro-1H-cyclopenta[c]oxonin-3(4H)-one

Following the general procedure as described in Example 1, [1,1'-bi(cyclopentan)]-1'-en-2-one (1.64 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (1.73 g, 83% yield). Single Z-isomer.

$^1$H NMR (300 MHz, CDCl$_3$): δ=4.78-4.65 (m, 1H), 2.85-2.57 (m, 2H), 2.41-2.08 (m, 5H), 2.05-1.88 (m, 3H), 1.73-1.60 (m, 3H), 1.58 (s, 3H), 1.27 (d, J=6.1 Hz, 3H) ppm. Two diastereomers: Major isomer: $^{13}$C NMR (75 MHz, CDCl$_3$): δ=173.9 (s), 138.8 (s), 128.0 (s), 71.2 (d), 49.3 (d), 32.8 (t), 32.7 (t), 30.5 (t), 29.8 (t), 23.6 (t), 23.0 (t), 19.3 (q), 18.5 (q) ppm. GC/MS (EI): 208 (M$^+$, 23), 164 (28), 146 (52), 135 (17), 121 (58), 108 (94), 93 (100), 79 (36), 67 (18), 55 (16), 41 (21). IR (neat, ν/cm$^{-1}$): 2948, 2871, 1736, 1448, 1143, 1073. HRMS (ESI): m/z: calcd. for C$_{13}$H$_{20}$O$_2$ (M+Na)$^+$ 231.1361. Found: 231.1359.

EXAMPLE 8 rac-(E)-14,16-Dimethyloxacyclohexadec-13-en-2-one

Following the general procedure as described in Example 1, 2-(prop-1-en-2-yl)cyclododecanone (2.22 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (2.34 g, 88% yield). Mixture of E/Z isomers in a ratio of 8:1.

$^1$H NMR (300 MHz, CDCl$_3$): δ=5.23-5.02 (m, 2H), 2.34-2.18 (m, 3H), 2.17-2.03 (m, 1H), 2.01-1.88 (m, 1H), 1.79-1.50 (m, 2H), 1.61 (s, 3H), 1.46-1.17 (m, 18H) ppm. Major isomer: $^{13}$C NMR (75 MHz, CDCl$_3$): δ=173.5 (s), 131.1 (s), 127.9 (d), 68.5 (d), 46.5 (t), 33.6 (t), 28.9 (t), 27.2 (t), 26.6 (t), 26.5 (d), 26.4 (t), 26.3 (t), 25.3 (t), 24.8 (t), 23.1 (t), 20.7 (q), 16.9 (q) ppm. GC/MS (EI): 266 (M$^+$, 28), 251 (4), 237 (3), 223 (6), 195 (2), 182 (3), 164 (4), 137 (4), 123 (18), 109 (25), 95 (100), 82 (75), 67 (37), 55 (43), 41 (34). IR (neat, ν/cm$^{-1}$): 2927, 2856, 1730, 1459, 1375, 1172, 1130. HRMS (ESI): m/z: calcd. for C$_{17}$H$_{30}$O$_2$ (M+Na)$^+$ 289.2143. Found: 289.2114.

EXAMPLE 9

(S)-1-((1R,2S,6R)-3,7,7-Trimethylbicyclo[4.1.0]hept-3-en-2-yl)ethyl acetate

Following the general procedure as described in Example 1, 1-(4,7,7-trimethylbicyclo[4.1.0]hept-4-en-3-yl)ethanone (1.78 g, 10 mmol), acetaldehyde (0.53 g, 12 mmol) and boron trifluoride etherate (0.14 g, 1.0 mmol) in 1,2-dichloroethane (10 mL) were reacted to give the title product as a colorless liquid (1.82 g, 82% yield).

$^1$H NMR (300 MHz, CDCl$_3$): δ=5.44-5.36 (m, 1H), 5.31-5.20 (m, 1H), 2.41-2.27 (m, 1H), 2.25-2.17 (m, 1H), 2.11-2.05 (m, 1H), 2.02 (s, 3H, acetyl-CH3), 1.66 (s, 3H, CH3), 1.22 (d, J=6.5 Hz, 3H), 1.02 (s, 3H, CH3), 0.86 (s, 3H, CH3), 0.71 (dd, J=8.7, 8.7 Hz, 1H), 0.58 (d, J=9.1 Hz, 1H) ppm. $^{13}$C NMR (75 MHz, CDCl$_3$): δ=170.4 (s), 131.2 (s), 120.4 (d), 73.5 (d), 39.9 (d), 29.2 (q), 23.5 (q), 23.2 (t), 21.8 (t), 21.3 (q), 18.0 (d), 16.4 (q), 16.3 (s), 13.6 (q) ppm.

GC/MS (EI): 222 (M$^+$, 1), 162 (13), 147 (23), 133 (8), 119 (78), 105 (18), 93 (100), 77 (14), 65 (4), 43 (75). IR (neat, ν/cm$^{-1}$): 2938, 2866, 1735, 1450, 1370, 1237. HRMS (ESI): m/z: calcd. for C$_{14}$H$_{22}$O$_2$ (M+Na)$^+$ 245.1517. Found: 245.1498.

Odour description: floral, agrestic, a bit woody, Nopyl Acetate-like, slight piny

EXAMPLE 10

2,3-Dimethylundec-2-en-5-yl acetate

Following the general procedure as described in Example 1, 3,3,4-trimethylpent-4-en-2-one (1.26 g, 10 mmol), heptanal (1.37 g, 12 mmol) and boron trifluoride etherate (0.14 g, 1.0 mmol) in 1,2-dichloroethane (10 mL) were reacted to give the title product as a colorless liquid (2.18 g, 91% yield).

$^1$H NMR (300 MHz, CDCl$_3$): δ=5.04-4.93 (m, 1H), 2.38 (dd, J=8.0, 13.6 Hz, 1H), 2.13 (dd, J=5.6, 13.6 Hz, 1H), 1.99 (s, 3H, acetyl-CH3), 1.67 (s, 3H, CH3), 1.66 (s, 3H, CH3), 1.63 (s, 3H, CH3), 1.57-1.45 (m, 2H), 1.38-1.20 (m, 8H), 0.88 (t, J=6.2 Hz, 3H, —CH2CH3) ppm. $^{13}$C NMR (75 MHz, CDCl$_3$): δ=170.6 (s), 127.0 (s), 123.8 (s), 73.4 (d), 39.4 (t), 34.2 (t), 31.7 (t), 29.2 (t), 25.5 (t), 22.5 (t), 21.1 (q), 20.6 (q), 20.5 (q), 19.0 (q), 14.0 (q) ppm. GC/MS (EI): 240 (M$^+$, 1), 180 (53), 165 (8), 151 (2), 137 (18), 123 (14), 109 (64), 95 (38), 83 (40), 67 (28), 55 (32), 43 (100). IR (neat, v/cm$^{-1}$): 2928, 2859, 2914, 1736, 1458, 1374, 1240. HRMS (ESI): m/z: calcd. for $C_{15}H_{28}O_2$ (M+Na)$^+$ 263.1987. Found: 263.1975.

EXAMPLE 11

N-(4,5-dimethylhex-4-en-2-yl)-N-methoxyacetamide

An argon flushed three-necked flask which was cooled by an ice-water bath was charged with 3,3,4-trimethylpent-4-en-2-one (0.50 g, 3.96 mmol), acetaldehyde O-methyl oxime (0.35 g, 4.75 mmol), and SnCl$_4$ (1.24 g, 4.75 mmol) in 1,2-dichloroethane (40 ml). The mixture was stirred for 48 hours at room temperature. The completion of reaction was checked by GC analysis of reaction aliquots quenched with a solution of saturated NaHCO$_3$ in water. After complete conversion, the reaction mixture was quenched with sat. aqueous NaHCO$_3$ solution (10 mL). The organic phase was separated and the aqueous layer was extracted with MTBE three times. The combined organic layers were washed with brine (20 mL), dried (MgSO$_4$) and evaporated in vacuo. The crude product was purified by distillation under reduced pressure to yield 0.76 g of the title product as colorless liquid (97%).

$^1$H NMR (300 MHz, CDCl$_3$): δ=4.72-4.52 (m, 1H), 3.76 (s, 3H), 2.41 (dd, J=13.2 Hz, 7.2 Hz, 1H), 2.20 (dd, J=13.2 Hz, 7.2 Hz, 1H), 2.09 (s, 3H), 1.68 (s, 3H), 1.64 (s, 3H), 1.63 (s, 3H), 1.23 (d, J=6.9 Hz, 3H); $^{13}$C NMR (75 MHz, CDCl$_3$): δ=173.5 (s), 127.1 (s), 124.4 (s), 64.5 (q), 52.6 (d), 38.5 (t), 20.6 (q), 20.6 (q), 20.5 (q), 18.6 (q), 17.7 (q); IR (neat, v/cm$^{-1}$): 2980, 2921, 1671, 1444, 1372, 1316, 1032 cm$^{-1}$; GC/MS (EI): m/z (%): 199 (1) [M$^+$], 110 (32), 95 (11), 74 (100), 55 (9), 43 (20); HRMS (ESI): m/z calcd for C$_{11}$H$_{21}$NO$_2$+H$^+$: 200.1645; [M+H$^+$]. found: 200.1640.

EXAMPLE 12

N-(2,3-dimethyldec-2-en-5-yl)-N-methoxyacetamide

Following the general procedure as described in Example 11, 3,3,4-trimethylpent-4-en-2-one (0.50 g, 3.96 mmol), hexanal O-methyl oxime (0.62 g, 4.75 mmol), and SnCl$_4$ (1.24 g, 4.75 mmol) in 1,2-dichloroethane (40 ml) were reacted to give the title product as a colorless liquid (0.47 g, 47% yield).

$^1$H NMR (300 MHz, CDCl$_3$): δ=4.50-4.35 (m, 1H), 3.72 (s, 3H), 2.46 (dd, J=13.2 Hz, 7.8 Hz, 1H), 2.17 (dd, J=13.2 Hz, 6.6 Hz, 1H), 2.10 (s, 3H), 1.66 (s, 3H), 1.62 (s, 6H), 1.48-1.31 (m, 8H), 0.88 (t, J=6.0 Hz, 3H); $^{13}$C NMR (75 MHz, CDCl$_3$): δ=173.8 (s), 127.0 (s), 124.7 (s), 64.1 (q), 57.7 (d), 37.7 (t), 32.0 (t), 31.8 (t), 26.5 (t), 22.6 (t), 20.8 (q), 20.6 (q), 20.6 (q), 18.7 (q), 14.1 (q); IR (neat, v/cm$^{-1}$): 2928, 2860, 1670, 1372 cm$^{-1}$; GC/MS (EI): m/z (%): 255 (1) [M$^+$], 166 (25), 142 (3), 130 (100), 100 (12), 83 (5), 67 (3), 55 (10), 43 (20); HRMS (ESI): m/z calcd for C$_{15}$H$_{29}$NO$_2$+H$^+$: 256.2271; [M+H$^+$]. found: 256.2288.

EXAMPLE 13

N-(4,5-dimethylhex-4-en-2-yl)-N-ethoxyacetamide

Following the general procedure as described in Example 11, 3,3,4-trimethylpent-4-en-2-one (0.50 g, 3.96 mmol), acetaldehyde O-ethyl oxime (0.41 g, 4.75 mmol), and SnCl$_4$ (1.24 g, 4.75 mmol) in 1,2-dichloroethane (40 ml) were reacted to give the title product as a colorless liquid (0.75 g, 89% yield).

$^1$H NMR (300 MHz, CDCl$_3$): δ=4.70-4.50 (m, 1H), 3.92 (q, J=6.3 Hz, 2H), 2.42 (dd, J=13.2 Hz, 7.2 Hz, 1H), 2.20 (dd, J=13.2 Hz, 7.5 Hz, 1H), 2.08 (s, 3H), 1.68 (s, 3H), 1.63 (s, 6H), 1.26 (t, J=7.2 Hz, 3H), 1.21 (d, J=6.9 Hz, 3H); $^{13}$C NMR (75 MHz, CDCl$_3$): δ=173.4 (s), 127.0 (s), 124.4 (s), 72.4 (t), 52.6 (d), 38.6 (t), 20.7 (q), 20.6 (q), 20.5 (q), 18.6 (q), 17.7 (q), 13.4 (q); IR (neat, v/cm$^{-1}$): 2980, 2932, 1669, 1373, 1033 cm$^{-1}$; GC/MS (EI): m/z (%): 213 (1) [M$^+$], 130 (11), 110 (24), 88 (100), 60 (9), 43 (17).

EXAMPLE 14

N-methoxy-N-(2,6,7-trimethylocta-2,6-dien-4-yl) acetamide

Following the general procedure as described in Example 11, 3,3,4-trimethylpent-4-en-2-one (0.50 g, 3.96 mmol), 3-methylbut-2-enal O-ethyl oxime (0.54 g, 4.75 mmol), and EtAlCl$_2$ (0.60 g, 4.75 mmol) in 1,2-dichloroethane (40 ml) were reacted to give the title product as a colorless liquid (0.30 g, 32% yield).

$^1$H NMR (300 MHz, CDCl$_3$): δ=5.30 (d, J=9.0 Hz, 1H), 5.23-5.08 (m, 1H), 3.72 (s, 3H), 2.55 (dd, J=13.2 Hz, 7.5 Hz, 1H), 2.18 (dd, J=13.2 Hz, 6.9 Hz, 1H), 2.06 (s, 3H), 1.73 (s, 3H), 1.67 (s, 6H), 1.63 (s, 3H), 1.60 (s, 3H); $^{13}$C NMR (75 MHz, CDCl$_3$): δ=172.0 (s), 135.5 (s), 127.1 (s), 123.8 (s), 122.8 (d), 64.2 (q), 54.2 (d), 37.7 (t), 25.5 (q), 20.5 (q), 20.3 (q), 20.3 (q), 18.8 (q), 18.6 (q); IR (neat, v/cm$^{-1}$): 2970, 2914, 2862, 1665, 1375, 986 cm$^{-1}$; GC/MS (EI): m/z (%): 239 (1) [M$^+$], 156 (42), 135 (6), 114 (100), 83 (15), 67 (6), 55 (12), 44 (18); HRMS (ESI): m/z calcd for C$_{11}$H$_{21}$NO$_2$+H$^+$: 240.1958; [M+H+]. found: 240.1962.

EXAMPLE 15

N-(3,4-dimethyl-1-phenylpent-3-en-1-yl)-N-methoxyacetamide

Following the general procedure as described in Example 11, 3,3,4-trimethylpent-4-en-2-one (0.50 g, 3.96 mmol), benzaldehyde O-methyl oxime (0.64 g, 4.75 mmol), and SnCl$_4$ (1.24 g, 4.75 mmol) in 1,2-dichloroethane (40 ml) were reacted to give the title product as a colorless liquid (0.40 g, 39% yield).

$^1$H NMR (300 MHz, CDCl$_3$): δ=7.46 (d, J=6.6 Hz, 2H), 7.36-7.28 (m, 3H), 5.80-5.50 (m, 1H), 3.28 (s, 3H), 3.13 (dd, J=13.5 Hz, 6.6 Hz, 1H), 2.45 (dd, J=13.5 Hz, 5.4 Hz, 1H), 2.08 (s, 3H), 1.69 (s, 3H), 1.64 (s, 3H), 1.61 (s, 3H); $^{13}$C NMR (75 MHz, CDCl$_3$): δ=172.8 (s), 139.7 (s), 128.5 (d), 128.5 (d), 128.3 (d), 128.3 (d), 127.9 (s), 127.7 (d), 123.8 (s), 64.3 (q), 58.4 (d), 35.0 (t), 20.8 (q), 20.5 (q), 20.5 (q), 18.6 (q); IR (neat, v/cm$^{-1}$): 2916, 1667, 1372, 988, 708 cm$^{-1}$; GC/MS (EI): m/z (%): 261 (1) [M$^+$], 130 (100), 109 (6), 100 (19), 91 (2), 81 (12), 67 (13), 55 (23), 41 (13).

EXAMPLE 16

1-(2-(2,3-dimethylbut-2-en-1-yl)indolin-1-yl)ethanone

Following the general procedure as described in Example 11, 3,3,4-trimethylpent-4-en-2-one (0.50 g, 3.96 mmol), 1H-indole (0.56 g, 4.75 mmol) which was in situ isomerized to 3H-indole, and SnCl$_4$ (1.24 g, 4.75 mmol) in 1,2-dichloroethane (40 ml) were reacted to give the title product as a white solid (0.56 g, 58%).

$^1$H NMR (300 MHz, DMSO-d$_6$): δ=7.98 (d, J=7.8 Hz, 1H), 7.25 (d, J=7.2 Hz, 1H), 7.16 (t, J=7.5 Hz, 1H), 7.01 (t, J=7.5 Hz, 1H), 4.61 (q, J=7.5 Hz, 1H), 3.19 (dd, J=15.6 Hz, 8.1 Hz, 1H), 2.62 (d, J=15.6 Hz, 1H), 2.36-2.08 (m, 5H), 1.69 (s, 3H), 1.63 (s, 3H), 1.49 (s, 3H); $^{13}$C NMR (75 MHz, DMSO-d$_6$): δ=167.7 (s), 141.8 (s), 131.1 (s), 127.7 (s), 126.8 (d), 124.9 (d), 123.4 (d), 123.3 (s), 117.1 (d), 59.0 (d), 38.5 (t), 33.1 (t), 22.9 (q), 20.5 (q), 20.2 (q), 18.5 (q); IR (neat, v/cm$^{-1}$): 2918, 1651, 1403, 769 cm$^{-1}$; GC/MS (EI): m/z (%): 243 (8) [M$^+$], 160 (22), 130 (2), 118 (100), 106 (1), 91 (7), 77 (1), 65 (1), 55 (2), 43 (5); HRMS (ESI): m/z calcd for C$_{16}$H$_{21}$NO+H$^+$: 244.1696; [M+H$^+$]. found: 244.1694.

EXAMPLE 17

(E)-1-methoxy-8,10-dimethyl-3,4,5,6,9,10-hexahydroazecin-2(1H)-one

An argon flushed three-necked flask which was cooled by an ice-water bath was charged with 2-(prop-1-en-2-yl)cyclohexanone (0.88 g, 6.38 mmol), acetaldehyde O-methyl oxime (0.56 g, 7.65 mmol), and SnCl$_4$ (1.66 g, 6.38 mmol) in 1,2-dichloroethane (65 ml). The mixture was stirred for 48 hours at room temperature. The completion of reaction was checked by GC analysis of reaction aliquots quenched with a solution of saturated NaHCO$_3$ in water. The reaction mixture was quenched with sat. aqueous NaHCO$_3$ solution (50 mL). The organic phase was separated and the aqueous layer was extracted with MTBE three times. The combined organic layers were washed with brine (30 mL), dried (MgSO$_4$) and evaporated in vacuo. The crude product was purified by distillation under reduced pressure to yield the title product as a colorless liquid (1.13 g, 84%).

$^1$H NMR (300 MHz, CDCl$_3$): δ=5.08 (t, J=6.9 Hz, 1H), 4.76-4.69 (m, 1H), 3.66 (s, 3H), 2.92-2.83 (m, 1H), 2.32-2.04 (m, 5H), 1.86-1.76 (m, 4H), 1.56 (s, 3H), 1.33 (d, J=17.7 Hz, 3H); $^{13}$C NMR (75 MHz, CDCl$_3$): δ=179.8 (s), 134.4 (s), 128.1 (d), 64.3 (q), 56.6 (d), 44.2 (t), 31.4 (t), 29.5 (t), 28.5 (t), 23.7 (t),18.1 (q), 17.3 (q); IR (neat, v/cm$^{-1}$): 2923, 2850, 1669, 1442, 1368, 1045 cm$^{-1}$; GC/MS (EI): m/z (%): 211 (8) [M], 180 (4), 130 (2), 165 (40, 138(23), 123 (15), 109 (100), 94 (11), 74 (37), 55 (11), 41 (15); HRMS (ESI): m/z calcd for C$_{12}$H$_{21}$NO$_2$+H$^+$: 212.1645; [M+H$^+$]. found: 212.1639.

Odour description: verbena fresh citrus grapefruit herbal, slightly bergamot, musky, agrumex aspect.

EXAMPLE 18

(E)-1-ethoxy-8,10-dimethyl-3,4,5,6,9,10-hexahydroazecin-2(1H)-one

Following the general procedure as described in Example 17, 2-(prop-1-en-2-yl)cyclohexanone (0.88 g, 6.38 mmol), acetaldehyde O-ethyl oxime (0.67 g, 7.65 mmol), and SnCl$_4$ (1.66 g, 6.38 mmol) in 1,2-dichloroethane (65 ml) were reacted to give the title product as a colorless liquid (1.14 g, 80% yield).

$^1$H NMR (300 MHz, CDCl$_3$): δ=5.11 (t, J=6.9 Hz, 1H), 4.77-4.70 (m, 1H), 3.85-3.77 (m, 2H), 2.93-2.84 (m, 1H), 2.30 (t, J=12.0 Hz, 1H), 2.22-2.04 (m, 4H), 1.87-1.76 (m, 4H), 1.56 (s, 3H), 1.28-1.23 (m, 6H); $^{13}$C NMR (75 MHz, CDCl$_3$): δ=179.8 (s), 134.2 (s), 128.0 (d), 72.2 (t), 56.4 (d), 44.3 (t), 31.6 (t), 29.4 (t), 28.4 (t), 23.7 (t), 18.1 (q), 17.2 (q), 13.3 (q); IR (neat, v/cm$^{-1}$): 2977, 2922, 1669, 1443, 1368, 1042 cm$^{-1}$; GC/MS (EI): m/z (%): 225 (5) [M$^+$], 165 (4), 138 (22), 123 (17), 109 (100), 88 (52), 67 (23), 55 (14), 40 (25).

EXAMPLE 19

(E)-1-methoxy-8-methyl-10-pentyl-3,4,5,6,9,10-hexahydroazecin-2(1H)-one

Following the general procedure as described in Example 17, 2-(prop-1-en-2-yl)cyclohexanone (0.88 g, 6.38 mmol), hexanal O-ethyl oxime (0.99 g, 7.65 mmol), and SnCl$_4$ (1.66 g, 6.38 mmol) in 1,2-dichloroethane (65 ml) were reacted to give the title product as a colorless liquid (1.00 g, 59% yield). E isomer>98%.

$^1$H NMR (300 MHz, CDCl$_3$): δ=5.03 (dd, J=9.0 Hz, 4.5 Hz, 1H), 4.49-4.43 (m, 1H), 3.58 (s, 3H), 2.84-2.75 (m, 1H), 2.23-1.96 (m, 5H), 1.75-1.71 (m, 4H), 1.48 (s, 3H), 1.38-1.25 (m, 8H), 0.83 (t, J=6.6 Hz, 3H); $^{13}$C NMR (75 MHz, CDCl$_3$): δ=180.4 (s), 134.0 (s), 128.0 (d), 63.9 (q), 61.8 (d), 42.5 (t), 32.2 (t), 31.9 (t), 31.6 (t), 29.5 (t), 28.6 (t), 26.9 (t), 23.8 (t), 22.6 (t), 17.3 (q), 14.0 (q); IR (neat, v/cm$^{-1}$): 2928, 2858, 1671, 1444, 1364,1206, 1011 cm$^{-1}$; GC/MS (EI): m/z (%): 267 (5) [M$^+$], 236 (3), 130 (69), 109 (100), 94 (17), 79 (21), 67 (23), 55 (18), 41 (22).

EXAMPLE 20

(E)-12-methyl-7,8,9,10,13a, 14-hexahydroazecino[1,2-a]indol-6(13H)-one

Following the general procedure as described in Example 17, 2-(prop-1-en-2-yl)cyclohexanone (0.88 g, 6.38 mmol), 1H-indole (0.90 g, 7.65 mmol) which was in situ isomerized to 3H-indole, and EtAlCl$_2$ (0.81 g, 6.38 mmol) in 1,2-dichloroethane (65 ml) were reacted to give the title product as a white solid (1.25 g, 77% yield).

$^1$H NMR (300 MHz, CDCl$_3$): δ=8.23 (d, J=7.8 Hz, 1H), 7.19-7.11 (m, 2H), 6.96 (t, J=7.5 Hz, 1H), 4.98-4.95 (m, 1H), 4.22 (t, J=9.6 Hz, 1H), 3.32 (dd, J=15.3 Hz, 9.6 Hz, 1H), 2.55 (d, J=9.6 Hz, 1H), 2.42-2.38 (m, 1H), 2.19-2.05 (m, 4H), 1.84 (d, J=12.9 Hz, 1H), 1.73 (s, 3H), 1.66-1.48 (m, 4H); $^{13}$C NMR (75 MHz, CDCl$_3$): δ=172.0 (s), 142.0 (s), 131.3 (d), 130.6 (s), 129.2 (s), 127.4 (d), 124.6 (d), 123.7 (d), 119.0 (d), 57.7 (d), 45.9 (t), 36.1 (t), 31.9 (t), 28.1 (t), 25.1 (t), 23.9 (t), 17.6 (q); IR (neat, v/cm$^{-1}$): 2915, 2857, 1642, 1396, 1269 cm$^{-1}$; GC/MS (EI): m/z (%): 255 (11) [M$^+$], 138 (4), 118 (100), 109 (11), 90 (9), 79 (7), 67 (7), 55 (4), 44 (6); HRMS (ESI): m/z calcd for C$_{17}$H$_{21}$NO+H$^+$: 256.1696; [M+H$^+$]. found: 256.1685.

EXAMPLE 21

(E)-1-methoxy-9,11-dimethylazacycloundec-8-en-2-one

Following the general procedure as described in Example 17, 2-(prop-1-en-2-yl)cycloheptanone (0.97 g, 6.38 mmol), acetaldehyde O-methyl oxime (0.56 g, 7.65 mmol), and SnCl$_4$ (1.66 g, 6.38 mmol) in 1,2-dichloroethane (65 ml) were reacted to give the title product as a colorless liquid (1.29 g, 90% yield).

$^1$H NMR (300 MHz, CDCl$_3$): δ=5.13 (dd, J=11.1 Hz, 3.9 Hz, 1H), 4.87-4.81 (m, 1H), 3.72 (s, 3H), 2.96 (dt, J=12.3 Hz, 3.3 Hz, 1H), 2.41 (t, J=12.3 Hz, 1H), 2.06-1.61 (m, 7H), 1.61 (s, 3H), 1.44-1.33 (m, 1H), 1.29 (d, J=6.9 Hz, 3H), 1.04-0.98 (m, 2H); $^{13}$C NMR (75 MHz, CDCl$_3$): δ=177.3 (s), 132.8 (s), 128.8 (d), 64.8 (q), 52.9 (d), 44.1 (t), 28.9 (t), 28.8 (t), 25.4 (t), 24.5 (t), 23.3 (t), 19.2 (q), 16.4 (q); IR (neat, v/cm$^{-1}$): 2974, 2933, 2857, 1667, 1378, 1044 cm$^{-1}$; GC/MS (EI): m/z (%): 225 (6) [M$^+$], 152 (16), 137 (15), 123 (14), 109 (94), 74 (67), 55 (22), 44 (100), 32 (53).

EXAMPLE 22

(E)-1-ethoxy-9,11-dimethylazacycloundec-8-en-2-one

Following the general procedure as described in Example 17, 2-(prop-1-en-2-yl)cycloheptanone (0.97 g, 6.38 mmol), acetaldehyde O-ethyl oxime (0.66 g, 7.65 mmol), and SnCl$_4$ (1.66 g, 6.38 mmol) in 1,2-dichloroethane (65 ml) were reacted to give the title product as a colorless liquid (1.11 g, 73% yield).

$^1$H NMR (300 MHz, CDCl$_3$): δ=5.16 (dd, J=11.1 Hz, 4.5 Hz, 1H), 4.87-4.81 (m, 1H), 3.92-3.82 (m, 2H), 3.01-2.92 (m, 1H), 2.44 (t, J=12.6 Hz, 1H), 2.05-1.54 (m, 8H), 1.61 (s, 3H), 1.28-1.24 (m, 6H), 1.07-1.04 (m, 2H); $^{13}$C NMR (75 MHz, CDCl$_3$): δ=177.3 (s), 132.6 (s), 128.7 (d), 72.7 (t), 52.7 (d), 44.1 (t), 28.9 (t), 28.7 (t), 25.4 (t), 24.5 (t), 23.3 (t), 19.2 (q), 16.3 (q), 13.4 (q); IR (neat, v/cm$^{-1}$): 2976, 2933, 1666, 1382, 1040 cm$^{-1}$; GC/MS (EI): m/z (%): 239 (9) [M$^+$], 152 (11), 137 (8), 123 (12), 109 (79), 88 (100), 67 (19), 55 (17), 41 (17).

EXAMPLE 23

(E)-1-methoxy-10-methyl-12-pentylazacyclododec-9-en-2-one

An argon flushed three-necked flask which was cooled by an ice-water bath was charged with 2-(prop-1-en-2-yl)cyclooctanone (1.50 g, 9.02 mmol), hexanal O-methyl oxime (1.56 g, 13.53 mmol), and SnCl$_4$ (2.35 g, 9.02 mmol) in 1,2-dichloroethane (90 ml). The mixture was stirred for 2 days at room temperature. The completion of reaction was checked by GC analysis of reaction aliquots quenched with a solution of saturated NaHCO$_3$ in water. The reaction mixture was quenched with sat. aqueous NaHCO$_3$ solution (50 mL). The organic phase was separated and the aqueous layer was extracted with MTBE three times. The combined organic layers were washed with brine (30 mL), dried (MgSO$_4$) and evaporated in vacuo. The crude product was purified by distillation to give the title product as a yellow oily liquid (2.38 g, 89%). E isomers>98%.

$^1$H NMR (300 MHz, CDCl$_3$): δ=5.05 (d, J=11.1 Hz, 1H), 4.82-4.74 (m, 1H), 3.74 (s, 3H), 2.98-2.88 (m, 1H), 2.40 (t, J=12.6 Hz, 1H), 2.16-1.92 (m, 5H), 1.60 (s, 3H), 1.60-1.31 (m, 12H), 1.20-1.04 (m, 3H), 0.89 (t, J=6.6 Hz, 3H); $^{13}$C NMR (75 MHz, CDCl$_3$): δ=175.3 (s), 131.2 (s), 128.0 (d), 65.1 (q), 54.8 (d), 42.7 (t), 33.9 (t), 31.9 (t), 28.9 (t), 26.6 (t), 25.1 (t), 25.0 (t), 24.4 (t), 23.5 (t), 22.8 (t), 22.7 (t), 16.1 (q), 14.2 (q); IR (neat, v/cm$^{-1}$): 2927, 2857, 1658, 1445, 1386 cm$^{-1}$; GC/MS (EI): m/z (%): 295 (13) [M$^+$], 264 (2), 166 (5), 130 (100), 109 (13), 95 (8), 81 (8), 67 (10), 55 (11), 41 (9); HRMS (ESI): m/z calcd for C$_{18}$H$_{33}$NO$_2$+H$^+$: 296.2584; [M+H$^+$]. found: 296.2585.

EXAMPLE 24

(E)-1-methoxy-10,12-dimethylazacyclododec-9-en-2-one

Following the general procedure as described in Example 23, 2-(prop-1-en-2-yl)cyclooctanone (1.50 g, 9.02 mmol), acetaldehyde O-methyl oxime (0.99 g, 13.53 mmol), and SnCl$_4$ (2.35 g, 9.02 mmol) in 1,2-dichloroethane (90 ml) were reacted to give the title product as a colorless liquid (1.91 g, 89% yield). E isomer>95%.

$^1$H NMR (300 MHz, CDCl$_3$): δ=5.06-4.96 (m, 2H), 3.76 (s, 3H), 2.98-2.88 (m, 1H), 2.41 (t, J=12.6 Hz, 1H), 2.20-1.89 (m, 5H), 1.63-1.44 (m, 7H), 1.29 (d, J=3.6 Hz, 3H), 1.30-1.07 (m, 3H); $^{13}$C NMR (75 MHz, CDCl$_3$): δ=174.4 (s), 131.2 (s), 127.9 (d), 65.5 (q), 49.7 (d), 44.4 (t), 28.6 (t), 24.9 (t), 24.8 (t), 24.1 (t), 23.2 (t), 22.6 (t), 19.9 (q), 15.9 (q); IR (neat, v/cm$^{-1}$): 2938, 2855, 1656, 1447, 1387 cm$^{-1}$; GC/MS (EI): m/z (%): 239 (20) [M$^+$], 192 (12), 166 (15), 151 (15), 123 (37), 109 (40), 74 (100), 55 (27), 41 (25).

EXAMPLE 25

(E)-1-ethoxy-10,12-dimethylazacyclododec-9-en-2-one

Following the general procedure as described in Example 23, 2-(prop-1-en-2-yl)cyclooctanone (1.50 g, 9.02 mmol), acetaldehyde O-ethyl oxime (1.18 g, 13.53 mmol), and SnCl$_4$ (2.35 g, 9.02 mmol) in 1,2-dichloroethane (90 ml) were reacted to give the title product as a colorless liquid (1.98 g, 87% yield). E isomer>96%.

$^1$H NMR (300 MHz, CDCl$_3$): δ=5.09-4.98 (m, 2H), 3.98-3.84 (m, 2H), 2.97-2.88 (m, 1H), 2.43 (t, J=12.6 Hz, 1H), 2.17-1.78 (m, 6H), 1.61 (s, 3H), 1.56-1.44 (m, 4H), 1.29-1.25 (m, 6H), 1.71-1.08 (m, 2H); $^{13}$C NMR (75 MHz, CDCl$_3$): δ=174.5 (s), 131.2 (s), 127.9 (d), 73.3 (t), 49.6 (d), 44.4 (t), 28.7 (t), 24.9 (t), 24.8 (t), 24.0 (t), 23.3 (t), 22.6 (t), 20.0 (q), 15.9 (q), 13.4 (q); IR (neat, v/cm$^{-1}$): 2977, 2935, 2856, 1656, 1440, 1385 cm$^{-1}$; GC/MS (EI): m/z (%): 253 (14) [M], 192 (9), 151 (8), 123 (20), 109 (23), 88 (100), 67 (19), 55 (17), 41 (16).

EXAMPLE 26

(E)-1-methoxy-14,16-dimethylazacyclohexadec-13-en-2-one

Following the general procedure as described in Example 23, 2-(prop-1-en-2-yl)cyclododecanone (2.00 g, 9.02 mmol), acetaldehyde O-methyl oxime (0.99 g, 13.53 mmol), and SnCl$_4$ (2.35 g, 9.02 mmol) in 1,2-dichloroethane (90 ml) were reacted to give the title product as a colorless liquid (2.33 g, 88% yield). Mixture of E/Z isomers in a ratio of 3:1.

$^1$H NMR (300 MHz, CDCl$_3$): δ=5.25-5.15 (m, 1H), 4.78-4.59 (m, 1H), 3.75 (s, 3H), 2.58-2.44 (m, 2H), 2.23-1.92 (m, 4H), 1.72-1.60 (m, 5H), 1.31-1.26 (m, 17H); $^{13}$C NMR (75 MHz, CDCl$_3$): δ=175.5 (s), 131.7 (s), 128.3 (d), 64.6 (q), 51.2 (d), 43.8 (t), 35.9 (t), 31.3 (t), 28.6 (t), 27.6 (t), 26.7 (t), 26.3 (t), 26.2 (t), 26.0 (t), 25.5 (t), 23.5 (t), 19.7 (q), 15.6 (q); IR (neat, v/cm$^{-1}$): 2926, 2855, 1664, 1443, 1383 cm$^{-1}$; GC/MS (EI): m/z (%): 295 (25) [M$^+$], 265 (15), 222 (14), 207 (47), 109 (24), 95 (52), 74 (97), 55 (70), 44 (100).

EXAMPLE 27

(E)-1-ethoxy-14,16-dimethylazacyclohexadec-13-en-2-one

Following the general procedure as described in Example 23, 2-(prop-1-en-2-yl)cyclododecanone (2.00 g, 9.02 mmol), acetaldehyde O-ethyl oxime (1.18 g, 13.53 mmol), and SnCl$_4$ (2.35 g, 9.02 mmol) in 1,2-dichloroethane (90 ml) were reacted to give the title product as a colorless liquid (2.45 g, 88% yield). Mixture of E/Z isomers in a ratio of 2:1.

$^1$H NMR (300 MHz, CDCl$_3$): δ=5.25-5.16 (m, 1H), 4.75-4.61 (m, 1H), 4.02-3.88 (s, 2H), 2.63-2.45 (m, 2H), 2.21-1.93 (m, 4H), 1.71-1.46 (m, 5H), 1.33-1.28 (m, 17H); $^{13}$C NMR (75 MHz, CDCl$_3$): δ=175.6 (s), 131.8 (s), 128.3 (d), 72.5 (t), 51.4 (d), 43.9 (t), 36.1 (t), 31.5 (t), 28.7 (t), 27.6 (t), 26.8 (t), 26.4 (t), 26.4 (t), 26.1 (t), 25.6 (t), 23.7 (t), 19.9 (q), 15.9 (q), 13.6 (q); IR (neat, v/cm$^{-1}$): 2926, 2856, 1664, 1443, 1384, 1030 cm$^{-1}$; GC/MS (EI): m/z (%): 309 (1) [M], 222 (7), 207 (7), 164 (5), 109 (10), 88 (100), 67 (20), 55 (29), 41 (20).

EXAMPLE 28

N-(2,4-dimethyl-1-phenyldec-2-en-5-yl)-N-methoxyformamide

Following the general procedure as described in Example 11, 2-benzyl-2-methylpent-3-enal (0.74 g, 3.96 mmol), hexanal O-methyl oxime (0.62 g, 4.75 mmol), and SnCl$_4$ (1.24 g, 4.75 mmol) in 1,2-dichloroethane (40 ml) were reacted to give the title product as a yellow liquid (0.70 g, 56% yield). Mixture of 4 isomers in a ratio of 2:2:3:3.

$^1$H NMR (300 MHz, CDCl$_3$): δ=8.53-7.83 (m, 1H), 7.29-7.13 (m, 5H), 5.24-4.98 (m, 1H), 4.07-3.48 (m, 4H), 3.30-3.11 (m, 2H), 2.90-2.65 (m, 1H), 1.66-1.29 (m, 11H), 1.06-0.89 (m, 6H); $^{13}$C NMR (75 MHz, CDCl$_3$): δ=158.7 (d), 139.8 (s), 136.2 (s), 128.9 (d), 128.6 (d), 128.3 (d), 128.3 (d), 128.1 (d), 126.0 (d), 65.8 (d), 62.8 (q), 37.9 (t), 35.2 (d), 31.6 (t), 28.7 (t), 26.2 (t), 22.5 (t), 18.6 (q), 16.3 (q), 14.0 (q); IR (neat, v/cm$^{-1}$): 2930, 1681, 1494, 1007, 699 cm$^{-1}$; GC/MS (EI): m/z (%): 317 (1) [M$^+$], 242 (7), 207 (7), 158 (100), 128 (16), 117 (21), 98 (36), 71 (25), 55 (13), 43 (30).

EXAMPLE 29

(4S,E)-1-butyl-4,7,8-trimethyl-10-propyl-3,4,5,6,9,10-hexahydroazecin-2(1H)-one

Following the general procedure as described in Example 17, 2,5-dimethyl-2-(prop-1-en-2-yl)cyclohexanone (1.06 g, 6.38 mmol), N-butylidenebutan-1-amine (0.97 g, 7.65 mmol), and SnCl$_4$ (1.66 g, 6.38 mmol) in 1,2-dichloroethane (65 ml) were reacted to give the title product as a colorless liquid (1.28 g, 76% yield). 3 isomers in a ratio of 1:2:8.

$^1$H NMR (300 MHz, CDCl$_3$): δ=3.57-3.40 (m, 2H), 2.73-2.66 (m, 1H), 2.60-2.40 (m, 3H), 1.91-1.62 (m, 10H), 1.50 (s, 3H), 1.47-1.20 (m, 9H), 1.04-0.89 (m, 7H); $^{13}$C NMR (75 MHz, CDCl$_3$): δ=173.2 (s), 132.3 (s), 123.9 (s), 56.1 (d), 43.0 (t), 38.6 (t), 36.1 (t), 34.3 (t), 33.6 (t), 33.4 (t), 31.5 (d), 29.8 (t), 25.7 (q), 20.9 (t), 20.9 (t), 20.2 (q), 19.0 (q), 14.0 (q), 14.0 (q); IR (neat, v/cm$^{-1}$): 2956, 2869, 1631, 1454, 1105, 730 cm$^{-1}$; GC/MS (EI): m/z (%): 293 (8) [M$^+$], 264 (5), 250 (6), 128 (100), 107 (4), 84 (10), 67 (6), 55 (7), 41 (8).

EXAMPLE 30

(E)-12-methyl-3,4,7,8,9,10,13,13a-octahydro-1H-pyrido[1,2-a]azecin-6(2H)-one

Following the general procedure as described in Example 17, 2-(prop-1-en-2-yl)cyclohexanone (0.88 g, 6.38 mmol), 2,3,4,5-tetrahydropyridine (0.64 g, 7.65 mmol), and SnCl$_4$ (1.66 g, 6.38 mmol) in 1,2-dichloroethane (65 ml) were reacted to give the title product as a colorless liquid (0.97 g, 69% yield).

$^1$H NMR (300 MHz, CDCl$_3$): δ=4.93-4.67 (m, 2H), 3.12 (dt, J=12.6 Hz, 3.0 Hz, 1H), 2.64-2.01 (m, 7H), 1.82-1.32 (m, 13H); $^{13}$C NMR (75 MHz, CDCl$_3$): δ=174.1 (s), 134.9 (s), 125.8 (d), 49.1 (d), 41.5 (t), 40.5 (t), 34.2 (t), 28.5 (t), 27.9 (t), 25.9 (t), 25.4 (t), 25.0 (t), 19.4 (t), 17.8 (q); IR (neat, v/cm$^{-1}$): 2937, 2917, 2852, 1638, 1407, 1245 cm$^{-1}$; GC/MS (EI): m/z (%): 221 (16) [M$^+$], 206 (2), 178 (4), 138 (5), 109 (7), 84 (100), 67 (8), 55 (12), 41 (8).

EXAMPLE 31

1-(2-(2,3-dimethylbut-2-en-1-yl)piperidin-1-yl)ethanone

Following the general procedure as described in Example 11, 3,3,4-trimethylpent-4-en-2-one (0.50 g, 3.96 mmol), 2,3,4,5-tetrahydropyridine (0.39 g, 4.75 mmol), and SnCl$_4$ (1.24 g, 4.75 mmol) in 1,2-dichloroethane (40 ml) were reacted to give the title product as a colorless liquid (0.24 g, 29%).

$^1$H NMR (300 MHz, CDCl$_3$): δ=4.87-4.55 (m, 1H), 3.96-3.58 (m, 1H), 3.20-2.63 (m, 1H), 2.49-2.04 (m, 6H), 1.81-1.37 (m, 13H); $^{13}$C NMR (75 MHz, CDCl$_3$): δ=169.0 (s), 127.3 (s), 124.4 (s), 53.0 (d), 36.7 (t), 35.2 (t), 29.1 (t), 25.4 (t), 21.1 (q), 20.5 (q), 20.5 (q), 19.4 (t), 19.1 (q); IR (neat, v/cm$^{-1}$): 2930, 2860, 1635, 1421, 1265, 997 cm$^{-1}$; GC/MS (EI): m/z (%): 209 (1) [M$^+$], 126 (48), 84 (100), 55 (7), 43 (7).

EXAMPLE 32 ethyl 3-(11-methyl-2-oxoazacyclotridec-10-en-1-yl)propanoate

An argon flushed flask was charged with 2-(prop-1-en-2-yl)cyclononanone (1.44 g, 8.0 mmol), imine ethyl 3-(methyleneamino)propanoate (2.58 g, 20.0 mmol) and 1,2-dichloroethane (40 mL). Ethylaluminum dichloride (8.89 mL, 1.8 M in toluene, 16 mmol) was added dropwise at room temperature. The mixture was stirred for 24 hours. The reaction mixture was quenched with sat. aqueous NaHCO3 solution (50 mL). The organic phase was separated and the aqueous layer was extracted with MTBE (50 mL*2). The combined organic layers were washed with brine (50 mL), dried (MgSO4) and evaporated in vacuo. The residue was purified by column chromatography on silica gel (MTBE/hexane=1:5) and give ethyl 3-(11-methyl-2-oxoazacyclotridec-10-en-1-yl)propanoate as a colorless liquid (2.15 g, 87% yield), E:Z=1:1. E isomer:a pair of rotamers (~1:1 ratio).

$^1$H NMR (mixture of rotamers, 300 MHz, CDCl3): δ=5.19-5.14 (m, 1H), 4.64-4.55 and 2.59-2.52 (m, 1H), 4.19-4.10 (m, 2H), 3.88-3.35 (m, 3H), 2.67-2.52 (m, 3H), 2.28-2.07 (m, 5H), 1.91-1.62 (m, 5H), 1.44-1.20 (m, 11H); $^{13}$C NMR (mixture of rotamers, 75 MHz, CDCl3): δ=173.3 (s), 173.3 (s), 172.3 (s), 171.2 (s), 132.4 (s), 131.4 (s), 129.7 (d), 127.8 (d), 60.9 (t), 60.5 (t), 46.5 (t), 41.6 (t), 41.5 (t), 40.2 (t), 38.3 (t), 37.5 (t), 33.3 (t), 32.7 (t), 32.6 (t), 29.8 (t), 27.6 (t), 27.6 (t), 27.1 (t), 27.0 (t), 26.7 (t), 26.5 (t), 26.1 (t), 26.0 (t), 25.1 (t), 25.0 (t), 24.3 (t), 23.1 (t), 17.0 (q), 15.7 (q), 14.2 (q), 14.1 (q); IR (neat): v=2926, 2855, 1732, 1642, 1421, 1373, 1180 cm-1; GC/MS (EI): m/z (%): 309 (1) [M$^+$], 294 (1), 264 (7), 222 (7), 130 (100), 84 (11), 55 (16), 42 (13); HRMS (ESI): m/z calcd. for C$_{18}$H$_{31}$NO$_3$+Na$^+$: 332.2196; [M+Na$^+$]. Found: 332.2212.

EXAMPLE 33

Catalyst Screening

Following the general procedure as described in Example 1, several catalysts have been used. Further details are given in Table 1, below. Yields are not optimized.

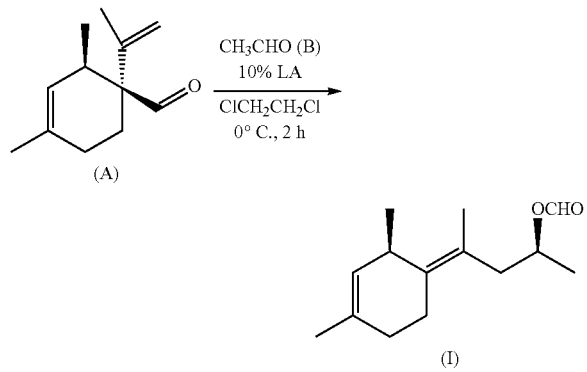

TABLE 1

Catalyst screening for the intermolecular electrocyclic rearrangement

| entry | Catalyst (10 mol %) | Conversion (%) | yield (%) |
|---|---|---|---|
| 1-1 | $BF_3OEt_2$ | >99 | 70 |
| 1-2 | $TiCl_4$ | >99 | 57 |
| 1-3 | $FeCl_3$ | >99 | 56 |
| 1-4 | $EtAlCl_2$ | 87 | 65 |
| 1-5 | p-TsOH—$H_2O$ | 68 | 46 |
| 1-6 | $SnCl_4$ | >99 | 51 |
| 1-7 | $AlCl_3$ | >99 | 52 |
| 1-8 | $H_2SO_4$ | >99 | 54 |

EXAMPLE 34

Catalyst Screening

Following the general procedure as described in Example 11, several catalysts have been used. Further details are given in Table 2, below. Yields are not optimized.

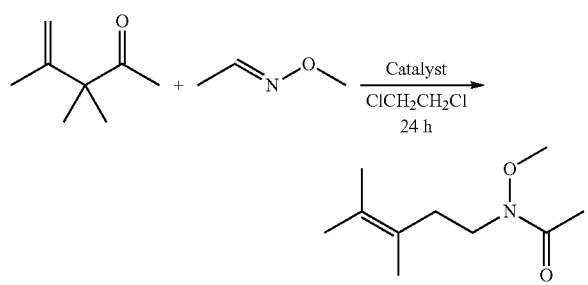

TABLE 2

Catalyst screening for the intermolecular electrocyclic rearrangement

| entry | Catalyst | amount of catalyst (mol %) | conversion [%] | yield (%) |
|---|---|---|---|---|
| 2-1 | $BF_3Et_2O$ | 100 | 99 | 96 |
| 2-2 | $SnCl_4$ | 100 | >99 | 97 |
| 2-3 | $SnCl_4$ | 50 | 93 | 91 |
| 2-4 | $SnCl_4$ | 20 | 68 | 65 |
| 2-5 | $TiCl_4$ | 100 | >99 | 81 |
| 2-6 | $EtAlCl_2$ | 100 | 80 | 78 |
| 2-7 | $AlCl_3$ | 100 | 82 | 80 |
| 2-8 | $FeCl_3$ | 100 | 97 | 92 |
| 2-9 | $CF_3SO_3H$ | 100 | >99 | 59 |

The invention claimed is:

1. A one step intermolecular electrocyclic rearrangement process comprising the step of reacting
   a. a beta, gamma-unsaturated aldehyde or ketone, wherein the beta, gamma-unsaturation is not part of an aromatic ring, with
   b. another aldehyde or a secondary aldimine in the presence of an acid.

2. The one step process according to claim 1 for the preparation of esters or lactones of homoallylic alcohols by direct acid catalyzed intermolecular electrocyclic rearrangement of
   a. a beta, gamma-unsaturated aldehyde or ketone, wherein the beta, gamma-unsaturation is not part of an aromatic ring, with
   b. another aldehyde.

3. The one step process according to claim 1 for the preparation of amides or lactames of homoallylic amines by direct acid catalyzed intermolecular electrocyclic rearrangement of
   a. a beta, gamma-unsaturated aldehyde or ketone, wherein the beta, gamma-unsaturation is not part of an aromatic ring, with
   b. a secondary aldimine.

4. The process according to claim 1 wherein the acid is a Lewis or Brønsted acid.

5. The process according to claim 1 wherein the other aldehyde is selected from a compound of the formula $R^6CO$ wherein $R^6$ is selected from $C_1$-$C_8$ alkyl, $C_2$-$C_8$ alkenyl and $C_6$-$C_8$ aryl, wherein the aryl is optionally substituted with one or more groups selected from methyl, methoxy, ethoxy, acetoxy, hydroxy, and 1,3-dioxol.

6. The process according to claim 1 wherein the other aldehyde is selected from acetaldehyde, propionaldehyde, isobutyraldehyde, butyraldehyde, pivalaldehyde, hexanal, heptanal, 3-methylbutanal, anisaldehyde, heliotropin and vanillin.

7. The process according to claim 1 wherein the secondary aldimine is selected from

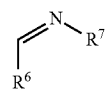

wherein
$R^6$ is selected from H, $C_1$-$C_8$ alkyl, $C_2$-$C_8$ alkenyl and $C_6$-$C_8$ aryl, wherein the aryl is optionally substituted with one or more groups selected from methyl, methoxy, ethoxy, acetoxy, hydroxy, and 1,3-dioxol;
$R^7$ is selected from $C_1$-$C_8$ alkyl, $C_6$-$C_8$ aryl, $C_1$-$C_2$ alkoxy, $C_1$-$C_8$ alkyl comprising one carbonyloxy group; or R⁶ and R⁷ form together with the atoms to which they are attached a 5-10 membered mono- or bi-cyclic ring.

8. The process according to claim 1 wherein the secondary aldimine is selected from acetaldehyde O-methyl oxime, acetaldehyde O-ethyl oxime, hexanal O-methyl oxime, hexanal O-ethyl oxime, 3-methylbut-2-enal O-ethyl oxime, benzaldehyde O-methyl oxime, 2,3,4,5-tetrahydropyridine, indole, 3,4-dihydro2H-pyrrole, N-butylidenebutan-1-amine, and ethyl 3-(methyleneamino) propanoate.

9. The process according to claim 1 wherein beta, gamma-unsaturated aldehydes or ketones is a compound of formula (A)

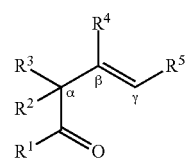

(A)

wherein

R¹ is selected from hydrogen, methyl and phenyl;

R² is selected from hydrogen, a hydrocarbon group selected from $C_1$-$C_8$ alkyl, $C_2$-$C_8$ alkenyl, $C_6$-$C_8$ aryl, and $C_1$-$C_3$ alkyl $C_6$-$C_8$ aryl, wherein the hydrocarbon group optionally comprises one functional group selected from —C(O)—, and —C(O)—;

R³ is selected from hydrogen and methyl;

or a) R¹ and R² or R¹ and R³ form together a bivalent linear $C_3$-$C_{16}$ alkyl or alkenyl chain, wherein the alkyl or alkenyl chain may be optionally substituted with one or more methyl or ethyl groups; or b) R² and R³ form together with the carbon atom to which they are attached a $C_5$-$C_8$ cycloalkyl ring or $C_5$-$C_8$ cycloalkenyl ring, wherein the ring is optionally substituted with one or more $C_1$-$C_4$ alkyl or alkenyl groups;

R⁴ is selected from hydrogen, methyl and ethyl;

R⁵ is selected from hydrogen, $C_1$-$C_5$ alkyl and $C_2$-$C_5$ alkenyl;

or a) R⁴ and R⁵ form together a bivalent $C_3$-$C_6$ alkyl or alkenyl; or b) R⁵ and R² or R⁵ and R³ form together with the carbon atoms to which they are attached a 5-12 membered hydrocarbon ring.

10. The process according to claim 2 wherein the other aldehyde is selected from a compound of the formula R⁶CO wherein R⁶ is selected from $C_1$-$C_8$ alkyl, $C_2$-$C_8$ alkenyl and $C_6$-$C_8$ aryl, wherein the aryl is optionally substituted with one or more groups selected from methyl, methoxy, ethoxy, acetoxy, hydroxy, and 1,3-dioxol.

11. The process according to claim 2 wherein the other aldehyde is selected from acetaldehyde, propionaldehyde, isobutyraldehyde, butyraldehyde, pivalaldehyde, hexanal, heptanal, 3-methylbutanal, anisaldehyde, heliotropin and vanillin.

12. The process according to claim 3 wherein the secondary aldimine is selected from

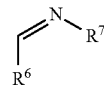

wherein

R⁶ is selected from H, $C_1$-$C_8$ alkyl, $C_2$-$C_8$ alkenyl and $C_6$-$C_8$ aryl, wherein the aryl is optionally substituted with one or more groups selected from methyl, methoxy, ethoxy, acetoxy, hydroxy, and 1,3-dioxol;

R⁷ is selected from $C_1$-$C_8$ alkyl, $C_6$-$C_8$ aryl, $C_1$-$C_2$ alkoxy, $C_1$-$C_8$ alkyl comprising one carbonyloxy group; or R⁶ and R⁷ form together with the atoms to which they are attached a 5-10 membered mono- or bi-cyclic ring.

13. The process according to claim 3 wherein the secondary aldimine is selected from acetaldehyde O-methyl oxime, acetaldehyde O-ethyl oxime, hexanal O-methyl oxime, hexanal O-ethyl oxime, 3-methylbut-2-enal O-ethyl oxime, benzaldehyde O-methyl oxime, 2,3,4,5-tetrahydropyridine, indole, 3,4-dihydro2H-pyrrole, N-butylidenebutan-1-amine, and ethyl 3-(methyleneamino) propanoate.

14. The process according to claim 2 wherein beta, gamma-unsaturated aldehydes or ketones is a compound of formula (A)

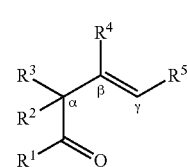

(A)

wherein

R¹ is selected from hydrogen, methyl and phenyl;

R² is selected from hydrogen, a hydrocarbon group selected from $C_1$-$C_8$ alkyl, $C_2$-$C_8$ alkenyl, $C_6$-$C_8$ aryl, and $C_1$-$C_3$ alkyl $C_6$-$C_8$ aryl, wherein the hydrocarbon group optionally comprises one functional group selected from —C(O)—, and —C(O)—;

R³ is selected from hydrogen and methyl;

or a) R¹ and R² or R¹ and R³ form together a bivalent linear $C_3$-$C_{16}$ alkyl or alkenyl chain, wherein the alkyl or alkenyl chain may be optionally substituted with one or more methyl or ethyl groups; or b) R² and R³ form together with the carbon atom to which they are attached a $C_5$-$C_8$ cycloalkyl ring or $C_5$-$C_8$ cycloalkenyl ring, wherein the ring is optionally substituted with one or more $C_1$-$C_4$ alkyl or alkenyl groups;

R⁴ is selected from hydrogen, methyl and ethyl;

R⁵ is selected from hydrogen, $C_1$-$C_5$ alkyl and $C_2$-$C_5$ alkenyl;

or a) R⁴ and R⁵ form together a bivalent $C_3$-$C_6$ alkyl or alkenyl; or b) R⁵ and R² or R⁵ and R³ form together with the carbon atoms to which they are attached a 5-12 membered hydrocarbon ring.

15. The process according to claim 3 wherein beta, gamma-unsaturated aldehydes or ketones is a compound of formula (A)

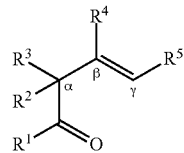

(A)

wherein
$R^1$ is selected from hydrogen, methyl and phenyl;
$R^2$ is selected from hydrogen, a hydrocarbon group selected from $C_1$-$C_8$ alkyl, $C_2$-$C_8$ alkenyl, $C_6$-$C_8$ aryl, and $C_1$-$C_3$ alkyl $C_6$-$C_8$ aryl, wherein the hydrocarbon group optionally comprises one functional group selected from —C(O)—, and —C(O)—;
$R^3$ is selected from hydrogen and methyl;
or
a) $R^1$ and $R^2$ or $R^1$ and $R^3$ form together a bivalent linear $C_3$-$C_{16}$ alkyl or alkenyl chain, wherein the alkyl or alkenyl chain may be optionally substituted with one or more methyl or ethyl groups; or
b) $R^2$ and $R^3$ form together with the carbon atom to which they are attached a $C_5$-$C_8$ cycloalkyl ring or $C_5$-$C_8$ cycloalkenyl ring, wherein the ring is optionally substituted with one or more $C_1$-$C_4$ alkyl or alkenyl groups;
$R^4$ is selected from hydrogen, methyl and ethyl;
$R^5$ is selected from hydrogen, $C_1$-$C_5$ alkyl and $C_2$-$C_5$ alkenyl;
or
a) $R^4$ and $R^5$ form together a bivalent $C_3$-$C_6$ alkyl or alkenyl; or
b) $R^5$ and $R^2$ or $R^5$ and $R^3$ form together with the carbon atoms to which they are attached a 5-12 membered hydrocarbon ring.

* * * * *